United States Patent [19]

Beversdorf et al.

[11] Patent Number: 4,658,085
[45] Date of Patent: Apr. 14, 1987

[54] HYBRIDIZATION USING CYTOPLASMIC MALE STERILITY, CYTOPLASMIC HERBICIDE TOLERANCE, AND HERBICIDE TOLERANCE FROM NUCLEAR GENES

[75] Inventors: Wallace D. Beversdorf, Guelph; Lawrence R. Erickson, Mississauga; Ian Grant, Guelph, all of Canada

[73] Assignee: University of Guelph, Guelph, Canada

[21] Appl. No.: 797,916

[22] Filed: Nov. 14, 1985

[51] Int. Cl.$^4$ .......................... A01H 1/02; A01H 5/00
[52] U.S. Cl. ........................................... 800/1; 47/58; 47/DIG. 1
[58] Field of Search .......................... 47/1, 58, DIG. 1

[56] References Cited

U.S. PATENT DOCUMENTS

| | | | |
|---|---|---|---|
| 3,842,538 | 10/1974 | Barabas | 47/58 |
| 4,045,912 | 9/1977 | Sun | 47/58 |
| 4,143,486 | 3/1977 | Maan | 47/58 |
| 4,351,130 | 9/1982 | Rutger et al. | 47/58 |
| 4,381,624 | 5/1983 | Laurence et al. | 47/58 |
| 4,443,971 | 4/1984 | Chaleff | 47/58 |
| 4,517,763 | 5/1985 | Beversdorf et al. | 47/58 |
| 4,535,060 | 8/1985 | Comai | 435/172.3 |
| 4,545,146 | 10/1985 | Davis | 47/58 |

FOREIGN PATENT DOCUMENTS

2139466A 11/1984 United Kingdom.

OTHER PUBLICATIONS

D. E. Falk, K. J. Kasha, and E. Reinbergs, Proceedings of the Fourth International Barley Genetics Symposium, Edinburgh, Jul. 22 to 29, 1981 (Edinburgh University Press), pp. 778 to 785.

Registration of a Shrunken Endosperm, Male-Sterile Germplasm to Facilitate Hybridization in Barley (Reg. No. GP 59), D. E. Falk and K. J. Kasha, Crop Science, vol. 22, Mar.-Apr., 1982, p. 450.

Highlights of Agriculture Research in Ontario, Dec., 1982, at pp. 18-19 in an article by W. D. Beversdorf and David J. Hume entitled "Canola: A New Oilseed Crop for Ontario."

Ontario Ministry of Agriculture and Food Factsheet No. 82-017, Feb., 1982, entitled "Spring Canola in Ontario" by D. J. Hume, R. J. McLaughlin, and W. D. Beversdorf.

I. Bartkowiak-Broda, P. Rousselle, and M. Renard (1979), "Investigation of Two Kinds of Cytoplasmic Male Sterility in Rape (*Brassica napus* L.)," Genet. Polon. 20:487-497.

Y. Ohkawa, T. Shiga, and T. Ishige (1979), "Male Sterility-Inducing-Cytoplasm in *Brassica campestris* var. *rapifera*," Annual Report, Division of Genetics, Dept. of Physiol and Genetics, Nat. Inst. of Agric. Sciences, Kannonadi, Yatabe, Tsukuba, Japan, pp. 30-31.

J. D. Palmer, C. R. Shields, D. B. Cohen, and T. J.

Orton (1983), "An Unusual Mitochondrial DNA Plasmid in the Genus *Brassica*," Nature 301:725-728.

P. Rousselle and M. Renard (1982), "Intérêt du Cultivar 'Bronowski' pour l'obtention de Plantes Male-Steriles Cytoplasmiques Chez le Colza (*Brassica napus* L.)," Agronomie 2 (19):951-956.

T. Shiga (1976), "Studies on Heterosis Breeding Using Cytoplasmic Male Sterility in Rapeseed, *Brassica napus* L.," Bull. Nat. Inst. Agric. Sci. Tokyo Series D. 27:75-85.

T. Shiga (1976), "Cytoplasmic Male Sterility and Its Utilization for Heterosis Breeding in Rapeseed, *Brassica napus* L.," JARO 10:177 $\propto$ 1182.

T. Shiga (1980), "Male Sterility and Cytoplasmic Differentiation," Chapter 12 in *Brassica* Crops and Wild Allies-Biology and Breeding, Japan Sci. Soc. Press, Tokyo, pp. 205-221.

K. F. Thomson (1972), "Cytoplasmic Male-Sterility in Oil-Seed Rape," Heredity 29(2): 253-257.

F. Vedel, C. Mathieu, P. Lebacq, F. Ambard-Bretteville, and R. Remy (1982), "Comparative Macromolecular Analysis of the Cytoplasms of Normal and Cytoplasmic Male Sterile *Brassica napus*," Theor. Appl. Genet. 62:255-262.

(List continued on next page.)

Primary Examiner—James R. Feyrer
Attorney, Agent, or Firm—Burns, Doane, Swecker & Mathis

[57] ABSTRACT

The process of the present invention provides a convenient route for producing a predetermined hybrid variety of a crop which is capable of undergoing both self-pollination and cross-pollination. Cytoplasmic male sterile plants which also exhibit cytoplasmic herbicide tolerance (i.e., to a Type A herbicide) and tolerance to a different herbicide attributable solely to nuclear genes (i.e., to a Type B herbicide) are the key plants for use in the present process. The maintainer and restorer plants exhibit tolerance to different herbicides (i.e., to either a Type A herbicide or a Type B herbicide). The economical bulk planting of the parent plants is made possible during each step of the process. For instance, cytoplasmic male sterile plants, plants resulting from the self-pollination of a maintainer, and restorer plants can be grown in a substantially random population, with the self-pollinated maintainer plants being destroyed by an appropriate herbicide prior to pollination, and the self-pollinated restorer plants being destroyed by an appropriate herbicide immediately following pollination or in the subsequent generation. The process of the present invention is applicable to grain crops, forage crops, seed-propagated fruits, seed-propagated ornamentals, and industrial species. In a particularly preferred embodiment a predetermined variety of *Brassica napus* (i.e., rape or improved forms thereof known as canola) is formed which is the product of cross-pollination.

79 Claims, No Drawings

OTHER PUBLICATIONS

"Transfer of Cytoplasmically-Inherited Triazene Resistance from Bird's Rape to Cultivated Oilseed Rape (*Brassica campestris* and *B. napus*)," by W. D. Beversdorf, J. Weiss-Lerman, L. R. Erickson, and V. Souza Machado appearing in the Canadian Journal of Genetics and Cytology, vol. XXII, No. 2, Jun. 1980, pp. 167–172.

"Uniparental Inheritance of Chloroplast Atrazine Tolerance in *Brassica Campestris*" by V. Souza Machado, J. E. Bandeen, G. R. Stephenson, and P. Lavigne, Can. J. Plant Sci. 58:977–981, 1978.

Amplification of the *aroA* Gene from *Escherichia coli* Results in Tolerance to the Herbicide Glyphosate", by S. G. Rogers, L. A. Brand, S. B. Holde, E. S. Sharps, and M. J. Brackin, Applied and Environmental Microbiology, 46(1):37–43 (1983).

"Herbicide-Resistant Mutants from Tobacco Cell Cultures", by R. S. Chaleff and T. B. Ray, Science, 223:1147–1150 (1984).

"Selection of Amitrole Tolerant Tobacco Calli and the Expression of this Tolerance in Regenerated Plants and Progeny", by S. R. Singer and C. N. McDaniel, Theor. Appl. Genet., 67:427–432 (1984).

"Selection of Glyphosate-Tolerant Tobacco Calli and the Expression of this Tolerance in Regenerated Plants" by S. R. Singer and C. N. McDaniel, Plant Physiol. 78:411–416 (1985).

"Cloning of Herbicide Resistance Into and Out of Plants", by B. J. Mazur, C. F. Chui, S. C. Falco, R. S. Chaleff and C. L. Mauvais, Biotech. '85 USA Outline Publications, pp. 97–108 (1985).

"Transfer of Cytoplasmically-Inherited Triazene Resistance from Bird's Rape Cultivated Oilseed Rape (*Brassica campestris* and *B. napus*)," by W. D. Beversdorf, J. Weiss-Lerman, L. R. Erickson, and V. Souza Machado appearing in the Canadian Journal of Genetics and Cytology, vol. XXII, No. 2, Jun. 1980, pp. 167–172.

1980 Germ Plasm Releases, Crop Science Department, Ontario Agricultural College, University of Guelph.

1983 Germ Plasm Releases, Crop Science Department, Ontario Agricultural College, University of Guelph.

"Registration of Triazine Resistant *Brassica Napus* Germplasm" (Reg. No. GP 2), W. D. Beversdorf, L. Weiss-Lerman, and L. R. Erickson, Crop Science, vol. 20, Mar.–Apr., 1980, p. 289.

HYBRIDIZATION USING CYTOPLASMIC MALE STERILITY, CYTOPLASMIC HERBICIDE TOLERANCE, AND HERBICIDE TOLERANCE FROM NUCLEAR GENES

BACKGROUND OF THE INVENTION

Plant scientists have recognized for many years that the hybridization of closely related plants may result in the production of offspring having a combination of desirable traits which previously were possessed separately by the parent plants. Also, hybrid plants of various crops commonly have possessed a vigor or heterosis which has contributed significantly to the crop yield and accordingly has been of considerable economic importance.

Since the plants selected for hybridization studies commonly are capable of undergoing both self-pollination and cross-pollination, the desired crossing often has been difficult to achieve on a reliable basis while operating on a commercially viable scale. Accordingly, controlled cross-pollination must be achieved in the substantial absence of self-pollination. A common technique heretofore utilized to accomplish this goal has been the use of cytoplasmic male sterile plants as the seed parent which are grown as a substantially uniform population adjacent to another substantially uniform population of plants from which the pollen is derived. Such technique has required precise control of the planting patterns, sufficient pollen transfer from one block of plants to another, and precise control of the seed harvest to preclude comingling of the two different seed products which are produced.

In U.S. Pat. No. 3,842,538 is disclosed a method of hybrid seed grain production wherein the bulk planting of cytoplasmic male sterile parent and the pollen parent is proposed. The seeds capable of forming hybrid plants are thereafter separated from the non-hybrid seeds on the basis of color. Such seed separation technique still would be tedious, however, and is not believed to have been commercially adopted. Articles by D. E. Falk, K. J. Kasha, and E. Reinbergs appearing in *Proceedings of the Fourth International Barley Genetics Symposium*, July 22 to 29, 1981, (Edinburgh University Press), pages 778 to 785, and by D. E. Falk and K. J. Kasha appearing in *Crop Science*, Vol. 22, March–April, 1982, page 450, discuss a tight linkage between genetic male sterility and a shrunken endosperm. See also, U.S. Pat. No. 4,351,130 which discloses a process for cereal production wherein tall male parents and short female parents can be grown in the same planting area, and after pollination the male parents are destroyed.

While considerable success has been realized in the past through the adoption of various well-known hybridization techniques, the need nevertheless has remained for alternate, less tedious, more efficient, or otherwise improved hybridization routes. Additionally, for many crops commercially feasible hybridization technology is yet to be implemented in spite of continuing research by dedicated plant scientists working around the world.

An example of a crop which is yet to benefit from the commercial availability of seed capable of growing hybrid plants is rape (i.e., *Brassica napus* or *Brassica campestris*). While not necessarily recognized by the general public, rape (and particularly high-quality forms thereof known as canola) is being grown as an increasingly important oilseed crop and a source of rapeseed meal in many parts of the world. The oil may serve as a high-quality vegetable oil and the meal may be used as a nutritious protein concentrate for livestock. The importance of rape as an agronomic crop is discussed in (1) *Highlights of Agricultural Research in Ontario*, December 1982, at pages 18–19 in an article by W. D. Beversdorf and David J. Hume, entitled "Canola: A New Oilseed Crop for Ontario," and in (2) The Ontario Ministry of Agriculture and Food Factsheet No. 82-017, February 1982, entitled, "Spring Canola in Ontario" by D. J. Hume, R. J. McLaughlin and W. D. Beversdorf.

Representative publications of researchers working in the area of rapeseed technology who have identified cytoplasmic male sterility in rape plants are identified below:

Bannerot, H., Boulidard, I., Cauderon, Y., and Tempe, J., "Cytoplasmic Male Sterility Transfer From Raphanus to Brassica" *Proc. Eucarpia Meeting Cruciferae Vegetable Crop*, Sect. 25:52–54 (1974).

Bartkowiak-Broda, I., Rousselle, P., and Renard, M., "Investigation of Two Kinds of Cytoplasmic Male Sterility in Rape (*Brassica napus L.*)," *Genet. Polon.* 20:487–497 (1979).

Ohkawa, Y., Shiga, T., and Ishige, T., "Male Sterility-Inducing-Cytoplasm in *Brassica campestris var*. rapifera", *Annual Report*, Division of Genetics, Dept. of Physiol. and Genetics, Nat. Inst. of Agric. Sciences, Kannondai, Yatabe, Tsukuba, Japan, pp. 30–31 (1979).

Palmer, J. D., Shields, C. R., Cohen, D. B., and Orton, T. J., "An Unusual Mitochondrial DNA Plasmid in the Genus Brassica" *Nature* 301:725–728 (1983).

Rousselle, P, and Renard, M., "Interet du cultivar<<-Bronowski>>pour l'obtention de plantes male-steriles cytoplasmiques chez le colza (*Brassica napus L.*)", *Agronomie* 2 (10):951–956 (1982).

Shiga, T., "Studies on Heterosis Breeding Using Cytoplasmic Male Sterility in Rapeseed., *Brassica napus L.*", *Bull. Nat. Inst. Agric. Sci.*, Tokyo Series D. 27:75–85 (1976).

Shiga, T., "Cytoplasmic Male Sterility and Its Utilization for Heterosis Breeding in Rapeseed (*Brassica napus L.*)", *JARQ* 10:177–182 (1976).

Shiga, T., "Male Sterility and Cytoplasmic Differentiation" Chapter 12 in *Brassica Crops and Wild Allies-Biology and Breeding*, Japan Sci. Soc. Press, Tokyo, pp. 205–221 (1980).

Thompson, K. F., "Cytoplasmic Male-Sterility in Oil-Seed Rape", *Heredity* 29(2):253–257 (1972).

Vedel, F., Mathieu, C., Lebacq, P., Ambard-Bretteville, F., and Remy, R., "Comparative Macromolecular Analysis of the Cytoplasms of Normal and Cytoplasmic Male Sterile *Brassica napus*" *Theor. Appl. Genet.* 62:255–262 (1982).

It has also been recognized in the past that weed control is an important consideration for those who choose to grow rape. Unchecked weeds will lessen the ultimate yield and can significantly reduce the quality by unavoidable contamination from diverse seeds which are harvested along with the desired crop. In order to deal with the weed problem various herbicide tolerant varieties of rape have been proposed so that unwanted weeds can be efficiently eliminated while growing in close proximity to the rape plants. See in this regard, "Transfer of Cytoplasmically-Inherited Triazine Resistance From Bird's Rape to Cultivated Oilseed Rape (*Brassica campestris* and *B. napus*)," by W. D. Beversdorf, J. Weiss-Lerman, L. R. Erickson and V. Souza Machado appearing in the *Canadian Journal of Genetics and Cytology,* Volume XXII, No. 2, June 1980, pages 167-172. See also "Uniparental Inheritance of Chloroplast Atrazine Tolerance in Brassica Campestris" by V. Souza Machado, J. D. Bandeen, G. R. Stephenson and P. Lavigne, *Can. J. Plant Sci.,* 58:977-981, 1978.

In our U.S. Pat. No. 4,517,763 entitled, "Hybridization Process Utilizing a Combination of Cytoplasmic Male Sterility and Herbicide Tolerance" is disclosed a hybridization process in which the bulk planting of the parents is made possible. This disclosure additionally was published as U.K. Patent Application No. GB 2,139,466A on Nov. 14, 1984.

It additionally has been recognized that plants can be identified by plant scientists which exhibit herbicide tolerance which is attributable soley to nuclear genes. See, for instance the following representative publications in this area:

Rogers, S. G., Braud, L. A., Holder, S. B., Sharps, E. S. and Brackin, M. J., "Amplification of the aroA Gene from Escherichia Coli Results in Tolerance to Herbicide Glyphosate", *Applied and Environmental Microbiology,* 46 (1):37-43 (1983).

Chaleff, R. S. and Ray, T. B., "Herbicide-Resistant Mutants From Tobacco Cell Cultures", *Science,* 223:1147-1150 (1984).

Singer, S. R. and McDaniel, C. N., "Selection of Amitrole Tolerant Tobacco Calli and the Expression of this Tolerance in Regenerated Plants and Progeny", *Theor. Appl. Genet.,* 67:427-432 (1984).

Singer, S. R. and McDaniel, C. N., "Selection of Glyphosate-Tolerant Tobacco Calli and the Expression of this Tolerance in Regenerated Plants", *Plant Physiol.,* 78:411-416 (1985).

Camai, L., U.S. Pat. No. 4,535,060, "Inhibition Resistant 5-Enolpyruvyl-3-Phosphoshickinate Synthetase, Production and Use" (1985).

See also our copending U.S. Ser. No. 797,917, filed concurrently herewith, entitled, "Hybridization Process Utilizing a Combination of Cytoplasmic Male Sterility and Herbicide Tolerance Attributable Solely to Nuclear Genes".

It is an object of the present invention to provide an improved hybridization process for use in forming a predetermined hybrid variety of a crop which is capable of undergoing both self-pollination and cross-pollination.

It is an object of the present invention to provide an improved hybridization process for use in forming a predetermined hybrid variety of a crop which is capable of undergoing both self-pollination and cross-pollination wherein the seed parent is cytoplasmic male sterile and various components of the hybrid production can be grown as bulk mixtures without the need for a precise planting pattern and the disadvantages associated therewith.

It is an object of the present invention to provide an improved hybridization process for use in forming a predetermined hybrid variety of a crop wherein cytoplasmic male sterile plants, self-pollinated maintainer plants, and restorer plants can be grown in a substantially random population without the need for precise planting patterns and the disadvantages associated therewith.

It is an object of the present invention to provide an improved hybridization process for use in forming a predetermined hybrid variety of a crop which is capable of undergoing both self-pollination and cross-pollination wherein the desired product may be formed on a reliable basis.

It is an object of the present invention to provide an improved hybridization process for use in forming a predetermined hybrid variety of a crop which is capable of undergoing both self-pollination and cross-pollination which is suitable for utilization on an economical basis on a commercially attractive scale.

It is an object of the present invention to provide an improved hybridization process for use in forming a predetermined hybrid variety of a crop which is capable of undergoing both self-pollination and cross-pollination wherein the desired product in a preferred embodiment additionally exhibits herbicide tolerance to at least two different types of herbicides which makes possible the selective destruction with ease of troublesome weeds growing within the hybrid crop area.

It is an object of the present invention to provide an improved hybridization process which particularly is suited for use when forming a predetermined hybrid variety of rape (e.g., *Brassica napus*), and to thereby provide a commercially practicable route for forming hybrid rape.

It is another object of the present invention to provide a new and useful *Brassica napus* seed product which is suitable for use when carrying out the process of the present invention.

It is a further object of the present invention to provide a *Brassica napus* seed product which is capable of forming $F_1$ hybrid rape plants which exhibits cytoplasmic tolerance to at least one herbicide, and tolerance to at least one different herbicide which is attributable solely to nuclear genes.

These and other objects and advantages will be apparent to those skilled in the art from reading of the following description and appended claims.

SUMMARY OF THE INVENTION

It has been found that an improved process for producing a substantially homogeneous population of plants of a predetermined hybrid variety of a crop which is capable of undergoing both self-pollination and cross-pollination comprises:

(a) growing in a first planting area a substantially random population of (1) cytoplasmic male sterile plants which exhibit cytoplasmic herbicide tolerance to at least one Type A herbicide and exhibit tolerance to at least one Type B herbicide which is attributable solely to homozygous dominant nuclear genes, and (2) male fertile plants which are homozygous recessive maintainer plants for the cytoplasmic male sterile plants and which lack the cytoplasmic herbicide tolerance to at least one Type A herbicide and exhibit tolerance to the at least one Type B herbicide attributable solely to the homozygous dominant nuclear genes, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of said first planting area, (c) growing in a second planting area a substantially random population of plants derived from seed harvested in step (b) together with homozygous dominant fertility restorer plants for the cytoplasmic male sterile plants which exhibit cytoplasmic herbicide tolerance to the at least one Type A herbicide and lack tolerance to said at least one Type B herbicide because of the absence of the required dominant nuclear genes for such trait, (d) contacting prior to pollination substantially all of the plants present in said second planting area with a Type A herbicide which is effective to destroy the plants resulting from seed formed on the maintainer plants in step (a) whereby cytoplasmic male sterile plants and restorer plants remain, (e) pollinating the cytoplasmic male sterile plants and the restorer plants of step (d) with pollen derived from the restorer plants and seed is formed on the cytoplasmic male sterile plants and on the restorer plants, (f) harvesting in bulk the seed which is formed on the plants remaining in the second planting area, (g) growing in a third planting area a substantially random population of plants derived from seed harvested in step (f), and (h) contacting substantially all of the plants present in said third planting area with a Type B herbicide which is effective to destroy the plants resulting from the seed formed on the restorer plants of step (e), whereby a substantially homogeneous population of male fertile $F_1$ hybrid plants of a predetermined variety is formed.

It has been found that an improved process for producing seed capable of forming a predetermined hybrid variety of a crop which is capable of undergoing both self-pollination and crosspollination comprises:

(a) growing in a first planting area a substantially random population of (1) cytoplasmic male sterile plants which exhibit cytoplasmic herbicide tolerance to at least one Type A type herbicide and exhibit tolerance to at least one Type B herbicide which is attributable solely to homozygous nuclear genes, and (2) male fertile plants which are homozygous recessive maintainer plants for the cytoplasmic male sterile plants and which lack the cytoplasmic herbicide tolerance to at least one Type A herbicide and exhibit tolerance to the at least one Type B herbicide attributable solely to the homozygous nuclear genes, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of the first planting area, (c) growing in a second planting area a substantially random population of plants derived from seed harvested in step (b) together with homozygous dominant fertility restorer plants for the cytoplasmic male sterile plants which exhibit cytoplasmic herbicide tolerance to the at least one Type A herbicide and lack tolerance to the at least one Type B herbicide because of the absence of the required nuclear genes for such trait, (d) contacting prior to pollination substantially all of the plants present in the second planting area with a Type A herbicide which is effective to destroy the plants resulting from seed formed on the maintainer plants in step (a) whereby cytoplasmic male sterile plants and restorer plants remain, (e) pollinating the cytoplasmic male sterile plants and the restorer plants of step (d) with pollen derived from the restorer plants, (f) subsequently contacting substantially all of the remaining plants present in the second planting area with a Type B herbicide which is effective to destroy the restorer plants and which is ineffective to destroy the cytoplasmic male sterile plants because of the herbicide tolerance attributable solely to the homozygous nuclear genes, and (g) harvesting seed from the cytoplasmic male sterile plants which is capable of forming $F_1$ hybrid plants which exhibit tolerance to said Type A and Type B herbicides in the substantial absence of seed from the maintainer and restorer plants which initially grew in the second planting area.

It has been found that an improved process for producing a substantially homogeneous population of plants of a predetermined hybrid variety of a crop which is capable of undergoing both self-pollination and cross-pollination comprises:

(a) growing in a first planting area a substantially random population of (1) cytoplasmic male sterile plants which exhibit cytoplasmic herbicide tolerance to at least one Type A type herbicide and exhibit tolerance to at least one Type B herbicide which is attributable solely to homozygous nuclear genes, and (2) male fertile plants which are homozygous recessive maintainer plants for the cytoplasmic male sterile plants and which exhibit the cytoplasmic herbicide tolerance to at least one Type A herbicide and lack the tolerance to the at least one Type B herbicide because of the absence of the required nuclear genes for such trait, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of the first planting area, (c) growing in a second planting area a substantially random population of plants derived from seed harvested in step (b) together with homozygous dominant fertility restorer plants for the cytoplasmic male sterile plants which lack said cytoplasmic herbicide tolerance to the at least one Type A herbicide and exhibit tolerance to the at least one Type B herbicide because of the presence of the required homozygous nuclear genes for such trait, (d) contacting prior to pollination substantially all of the plants present in the second planting area with a Type B herbicide which is effective to destroy the plants resulting from seed formed on the maintainer plants in step (a) whereby cytoplasmic male sterile plants and restorer plants remain, (e) pollinating the cytoplasmic male sterile plants and the restorer plants of step (d) with pollen derived from the restorer plants and seed is formed on the cytoplasmic male sterile plants and on the restorer plants, (f) harvesting in bulk the seed which is formed on the plants remaining in the second planting area, (g) growing in a third planting area a substantially random population of plants derived from seed harvested in step (f), and (h) contacting substantially all of the plants present in the third planting area with a Type A herbicide which is effective to destroy the plants resulting from the seed formed on the restorer plants of step (e), whereby a substantially homogeneous population of male fertile $F_1$ hybrid plants of a predetermined variety is formed.

It has been found that an improved process for producing seed capable of forming a predetermined hybrid variety of a crop which is capable of undergoing both self-pollinatin and crosspollination comprises:

(a) growing in a first planting area a substantially random population of (1) cytoplasmic male sterile plants which exhibit cytoplasmic herbicide tolerance to at least one Type A type herbicide and exhibit tolerance to at least one Type B herbicide which is attributable solely to homozygous nuclear genes, and (2) male fertile plants which are homozygous recessive maintainer plants for the cytoplasmic male sterile plants and which exhibit the cytoplasmic herbicide tolerance to at least one Type A herbicide and lack the tolerance to the at least one Type B herbicide because of the absence of the required nuclear genes for such trait, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of the first planting area, (c) growing in a second planting area a substantially random population of plants derived from seed harvested in step (b) together with homozygous dominant fertility restorer plants for the cytoplasmic male sterile plants which lack cytoplasmic herbicide tolerance to the at least one Type A herbicide and exhibit tolerance to the at least one Type B herbicide because of the presence of the required nuclear homozygous nuclear genes for such trait, (d) contacting prior to pollination substantially all of the plants present in said second planting area with a Type B herbicide which is effective to destroy the plants resulting from seed formed on the maintainer plants in step (a) whereby cytoplasmic male sterile plants and restorer plants remain, (e) pollinating the cytoplasmic male sterile plants and the restorer plants of step (d) with pollen derived from the restorer plants and seed is formed on the cytoplasmic male sterile plants and on the restorer plants, (f) subsequently contacting substantially all of the remaining plants present in the second planting area with a Type A herbicide which is effective to destroy the restorer plants and which is ineffective to destroy the cytoplasmic male sterile plants because of the herbicide tolerance attributable solely to the homozygous nuclear genes, and (g) harvesting seed from the cytoplasmic male sterile plants which is capable of forming $F_1$ hybrid plants in the substantial absence of seed from the maintainer and restorer plants which initially grew in the second planting area.

A *Brassica napus* seed product is provided consisting of a substantially homogeneous assemblage of seeds which upon growth yield rape plants which exhibit a combination of cytoplasmic male sterility, cytoplasmic tolerance to at least one herbicide, and tolerance to at least one different herbicide which is attributable solely to homozygous dominant nuclear genes.

A *Brassica napus* seed product is provided consisting of a substantially homogeneous assemblage of seeds which upon growth yield rape plants which exhibit a combination of cytoplasmic male sterility, cytoplasmic tolerance to at least one herbicide, and tolerance to at least one different herbicide which is attributable solely to homozygous recessive nuclear genes.

A *Brassica napus* seed product is provided consisting of a substantially homogeneous assemblage of seeds which upon growth yield male fertile $F_1$ hybrid rape plants which exhibit cytoplasmic tolerance to at least one herbicide, and tolerance to at least one different herbicide which is attributable solely to nuclear genes.

DESCRIPTION OF THE PREFERRED EMBODIMENTS

The hybridization concept of the present invention is deemed to be generally applicable for the formation of a predetermined variety of any crop which is capable of undergoing both self-pollination and cross-pollination. For the purposes of the present invention hybridization is deemed to occur when two parent plants which are not identical from the nuclear and cytoplasmic point of view are cross-pollinated. Seed capable of forming a hybrid plant is deemed to result from the fertilization of a cytoplasmic male sterile plant with pollen from a restorer plant which is capable of pollinating the same.

A predetermined hybrid variety of a grain crop, a forage crop, a seed-propagated fruit, a seed-propagated ornamental, or of an industrial species, etc., may be formed in accordance with the process of the present invention. For the purposes of the present invention grain crops are those which are grown primarily for seed, and forage crops are those which are grown primarily for the consumption of plant parts other than seed such as the foliage or other vegetative structure.

Representative grain crops which may be hybridized in accordance with the process of the present invention include cereals (e.g., wheat, oats, barley, rye, corn, triticale, sorghum, etc.), grain legumes (e.g., field beans, peas, peanuts, lentils), and oilseeds (e.g., flax, mustard, safflower, sunflower, soybeans, rape, etc.). Representative forage crops which may be hybridized in accordance with the process of the present invention include alfalfa, sugar beets, onions, peppers, seed-propagated potatoes, turnips, cabbage, broccoli, brome grass, etc. Representative seed-propagaged fruits which may be hybridized in accordance with the process of the present invention include tomatoes, peppers, watermelons, etc. Representative seed-propagated ornamentals which may be hybridized in accordance with the process of the present invention include petunias, marigolds, etc. Representative industrial species which may be hybridized in accordance with the process of the present invention include poplar trees, maple trees, cotton, fibre flax, tobacco, kelp, etc.

The process of the present invention is particularly suited for the formation of a hybrid variety of a crop of the family Brassicaceae, which is sometimes designated the Cruciferae family or the Mustard family. Within this family one may select with greater particularity a crop of the genus Brassica (e.g., a hybrid variety of rape plant classified as *Brassica napus* or *Brassica campestris*). Each of these previously named species occurs in a spring and winter (fall-seeded) type. High-quality forms of rapeseed which are used primarily as a source of vegetable oil and of rapeseed meal (a protein concentrate for livestock) are commonly referred to as canola. For instance, canola often identifies quality rapeseed which is low in erucic acid (less than 5%) and glucosinolates (less than 3 milligrams per gram of oil-free meal). Alternatively, rapeseed may be employed in the production of lubricants, paints, varnishes, and plastics in accordance with known technology.

When carrying out the process of the present invention, it is necessary to select female parent plants which exhibit a combination of cytoplasmic male sterility, cytoplasmic herbicide tolerance (i.e., tolerance to a Type A herbicide), and tolerance to a herbicide which is attributable solely to homozygous nuclear genes (i.e., tolerance to a Type B herbicide). For the purposes of the present invention a plant is considered to be male sterile when it is incapable of dehiscing functional pollen (i.e., is incapable of in situ fertilization of an egg). In all instances the male sterility must be manifest because of the specific type of cytoplasm which is present. It is essential that the cytoplasmic male sterile plants possess the ability to form seed which yields fully fertile hybrid plants following pollination from a pollen source which possesses homozygous dominant fertility restoring genes which are capable of interacting with the cytoplasm. The cytoplasmic male sterile plants will possess the ability to form seeds which yield cytoplasmic male sterile plants following pollination from a pollen source which lacks the dominant fertility-restoring genes.

For the purposes of the present invention a plant is considered to possess herbicide tolerance when it has the ability to withstand or to endure a given herbicide while carrying on its normal plant functions. In contrast, plants which lack such herbicide tolerance are significantly impaired or otherwise destroyed under the same conditions. Such lack of herbicide tolerance also can be manifest through the prevention of seed germination whereby the potential plant is destroyed at a very early stage in its development.

For the purposes of the present invention a plant is considered to possess cytoplasmic herbicide tolerance when its ability to withstand and endure a given herbicide while carrying on its normal plant functions (e.g., seed formation) can be traced to the nature of the cytoplasm of the plant. Herbicides for which such tolerance is manifest because of the nature of the plant cytoplasm are defined herein as Type A herbicides.

The mode of operation of the particular Type A herbicide employed in the process of the present invention can be varied widely so long as the required elimination of unwanted plants can be selectively accomplished without undue damage to the herbicide tolerant plants at the appropriate stage in the process. A Type A herbicide should be employed which is recognized to be safe for agricultural use. For instance it has been found that known agricultural herbicides which operate by inhibiting photosynthesis may be selected. However, Type A herbicides which function by other routes likewise may be selected so long as the desired controlled elimination of unwanted plants can be accomplished. Representative Type A herbicides are the s-triazines and the as-triazines. In a preferred embodiment with rape the Type A herbicide is atrazine (i.e., 2-chloro-4-ethylamino-6-isopropylamino-s-triazine). Alternatively, other representative Type A herbicides for use with rape are cyanazine (i.e., [[4-chloro-6-(ethylamino)-s-triazine-2-yl]amino]-2-methylpriionitrile) and metribuzin (i.e., 4-amino-6-tert-butyl-3-(methylthio)-as-triazine-5(4H)-one).

The Type A herbicide can be applied by conventional means prior to pollination or after pollination. Prior to pollination the Type A herbicide may be applied to seeds at the pre-emergence stage so as to prevent germination or to the young seedling plants at the post-emergence stage following germination (i.e., at a pre-anthesis stage). Alternatively, the Type A herbicide may be applied to older plants. The Type A herbicide may be applied to the entire plant or to plant parts, such as to the roots through the soil, to the leaves, to the stems, etc. For instance, when using atrazine as the Type A herbicide with rape, the herbicide conveniently may be applied as an aqueous foliar spray to the leaves and stems of the growing plants at a rate of approximately 0.5 to 4 kilograms per hectare (e.g., approximately 2 kilograms per hectare). The 2 kilograms per hectare rate of application of atrazine to *Brassica napus* plants has been found to be a safe and effective rate; however, a lesser application rate frequently may be used. A conventional emulsifier or oil optionally also may be present at the time of application. Alternatively, the Type A herbicide may be applied as solid granules directly to the plant or to the soil as will be apparent to those skilled in herbicide use.

For the purposes of the present invention a plant is considered to possess Type B herbicide tolerance when its ability to withstand and endure a given herbicide while carrying on its normal plant functions (e.g., seed formation) can be traced solely to the presence of nuclear genes. The cytoplasmic male sterile plants as well as either the maintainer or the restorer plants will preferably exhibit a Type B herbicide tolerance which is attributable solely to homozygous dominant nuclear genes. In some embodiments the Type B herbicide tolerance can be attributable solely to homozygous recessive nuclear genes. However, in the embodiment of the present process wherein the product of self-pollinated restorer plants is eliminated from among $F_1$ hybrid plants by the use of a Type B herbicide, it is essential that cytoplasmic male sterile plants and the maintainer plants exhibit Type B herbicide tolerance which is attributable solely to homozygous dominant nuclear genes. In the embodiment of the present process wherein restorer plants are eliminated by use of a B Type herbicide following pollination, the cytoplasmic male sterile plants and the maintainer plants can exhibit Type B herbicide tolerance which is attributable solely to homozygous recessive nuclear genes; however, the resulting seed will be capable of growing $F_1$ hybrid plants which lack said Type B herbicide tolerance. Also, in the embodiment of the present process wherein restorer plants are eliminated from among cytoplasmic male sterile plants by use of a Type A herbicide, the Type B herbicide tolerance present in the cytoplasmic male sterile and maintainer plants optionally may be attributable to homozygous recessive nuclear genes provided that there is no requirement that the final product also exhibit Type B herbicide tolerance. As will be apparent from the process steps described herein, it is essential that at least two different herbicides be selected for which the maintainer and restorer plants do not each exhibit tolerances which are of both a Type A and a Type B character.

The mode of operation of the Type B herbicide employed in the process of the present invention can be varied widely so long as the required elimination of unwanted plants can be selectively accomplished without undue damage to the herbicide tolerant plants at the appropriate stage in the process. A Type B herbicide should be employed which is recognized to be safe for agricultural use. The Type B herbicide employed when carrying out the process of the present invention may be selected from a wide variety of herbicide classes so long as it is used in conjunction with plants which possess the nuclear genes required to impart the necessary herbicide tolerance and provided such plants do not independently exhibit cytoplasmic herbicide tolerance for the same herbicide. Representative herbicides from which the Type B herbicide may be selected are as follows:

aliphatic carboxylics (e.g., trichloroacetic acid, dalapon, etc.), amides and acid amides (e.g., alachlor, metolachlor, etc.), benzoics (e g., dicamba, chloramben, etc.), bipyridyliums (e.g., paraquat, diquat, etc.), carbamates (e.g., barban, desmedipham, etc.), cyclohexenones (e.g., sethoxydim, etc.), dinitroanilines (e.g., trifluralin, oryzalin, etc.), diphenylethers (e.g., acifluorfen, nitrofen, etc.), glycine derivatives (e.g., glyphosate sometimes identified as phosphonomethyl glycine, etc.), imidazolinones (e.g., imazaquine, etc.), nitriles (e.g., bromoxynil, ioxynil, etc.) phenols (e.g., dinofeb, etc.), phenoxycarboxylics (e.g., 2, 4-D, MCPA, etc.), phenoxy-phenoxy and related compounds (e.g., diclofop, fluazifop), pyridines (e.g., picloram, clopyralid, etc.), pyrimidines (e.g., bromicil, terbicil, etc.), sulfonylureas (e.g., chlorsulfuron), thiocarbamates (e.g., EPTC, butylate, etc.), triazines (e.g. atrazine, simazine, metribuzin, etc.), ureas (e.g., diuron, linuron, etc.), amitrole, and bentazon.

In a preferred embodiment the Type B herbicide selected is chlorsulfuron which is believed to function by the inhibition of amino acid metabolism. Such herbicide is commercially available from DuPont Chemical Company under the GLEAN trademark. In a preferred embodiment the herbicide is glyphosate (phosphonomethyl glycine). Such herbicide is available commercially from Monsanto Corporation under the ROUNDUP trademark. Two other preferred Type B herbicides are amitrole and bentazon.

The Type B herbicide can be applied by conventional means prior to pollination or after pollination. Prior to pollination the herbicide may be applied to seeds at the pre-emergence stage so as to prevent germination or to the young seedling plants at the post-emergence stage following germination (i.e., at a pre-anthesis stage). Alternatively, the herbicide may be applied to older plants. The herbicide may be applied to the entire plant or to plant parts, such as to the roots through the soil, to the leaves, to the stems, etc. In most instances it is recommended that the herbicide be applied by spraying the foliage at rate specified by its manufacturer. However, the optimum application rate for a given herbicide can be determined by routine experimentation.

The key cytoplasmic male sterile female parent plants having tolerance to different Type A and Type B herbicides for use in the process of the present invention can be derived by any one of number of routes available to plant scientists. Commonly this is done by first selecting plants which have the requisite Type A herbicide tolerance which is attributable to the nature of the cytoplasm. This can be done by making selections from plants which have been subjected to a herbicide for an extended period of time, preferably for a number of generations. The natural selection process which has been found to occur in such surviving plants effectively leads plant researchers to those individual plants which inherently possess the requisite Type A herbicide tolerance. Subsequent testing can be carried out to identify clearly those individual plants which possess the requisite Type A herbicide tolerance and in which such tolerance can be attributed to the cytoplasm. During the selection process it is possible also to examine plants which are related but not in all respects analogous to the plant which is sought to be hybridized.

Once plants having the requisite Type A cytoplasmic herbicide tolerance are on hand, populations of these can be pollinated in a hybridization plant breeding program and observed and selected for those which dehisce no functional pollen. Via this route one may obtain the plants which exhibit the combination of cytoplasmic male sterility and cytoplasmic herbicide tolerance.

Other techniques which may be employed to yield such plants having a combination of cytoplasmic male sterility and Type A herbicide tolerance include the controlled introgression of the recessive genes for fertility restoration from available male steriles into the nucleus of a Type A herbicide tolerant line. Recently available biotechnology techniques may be applied such as protoplast fusion involving a herbicide tolerant line and a cytoplasmic male sterile line (see, for instance, International Publication WO84/03606), organelle transformation, and DNA transformation wherein both organelle and nuclear DNA are modified. Also, the mutagenesis of the cytoplasmic genome of the Type A herbicide tolerant line may be accomplished. Once the key plant having both cytoplasmic herbicide tolerance and cytoplasmic male sterility is located or synthesized, it may be multiplied so that its characteristics can be confirmed on a larger scale.

Commonly, male fertile plants having the requisite Type B herbicide tolerance attributable solely to nuclear genes are isolated, and such herbicide tolerance is next transferred to plants which possess the required cytoplasmic male sterility and Type A herbicide tolerance. For instance, large populations of plants can be subjected to a given herbicide to select plants which through a spontaneous genetic variation will possess the nuclear genes required to impart Type B herbicide tolerance. Alternatively, the required Type B herbicide tolerance can be developed through in vitro selection from a tissue culture medium which includes a Type B herbicide intended for use in the process. Such in vitro selection may be carried out using known technqiues at the protoplast level, the suspension culture level, the callus culture level, the micropore culture level, etc. Mutagens optionally can be employed to further encourage genetic variation within the plants being evaluated. Once the required genes are identified they can be transferred to the appropriate parent through the application of any one of a variety of techniques, such as by crossing or back-crossing, genetic engineering, etc. See, for instance, "Cloning of Herbicide Resistance Into and Out of Plants" by B. J. Mazur, C. F. Chui, S. C. Falco, R. S. Chaleff and C. J. Mauvais, Biotech '85 USA, Outline Publications, pp. 97–108 (1985), which is herein incorporated by reference. In all instances the nuclear source of the herbicide tolerance can be confirmed by observing the mode of transmission of the tolerance in subsequent generations. The agronomic character of herbicide tolerant plants commonly will be improved by hybridization and selection using standard plant breeding techniques.

Maintainer plants which are capable of pollinating the plants which exhibit cytoplasmic male sterility must, by necessity, be homozygous maintainers with respect to recessive fertility restorer genes which interact with the requisite cytoplasm. They also must possess either Type A herbicide tolerance or Type B herbicide tolerance, depending upon the process embodiment in which they are utilized. Suitable maintainer plants can be developed simultaneously with the search for the cytoplasmic male sterile plants since they commonly are necessary in order to easily confirm whether the desired cytoplasm is in fact present. The maintainer plants selected commonly are of substantially the same nuclear genotype as the cytoplasmic male sterile plants with the exception that they possess recessive fertility restorer genes and the possible exception that they lack the required nuclear genes for Type B herbicide tolerance. Controlled introgression of the recessive genes for fertility restoration from partial male steriles into fertile cytoplasms may be accomplished. Such partial male steriles are heterozygous since only half of the gametes produced are recessive for the fertility restoration gene. Male parents which have been found to induce cytoplasmic male sterility following wide hybridization may be tested for the presence of recessive genes for fertility restoration. Also, naturally recurring populations or currently grown cultivars may be evaluated by well-known techniques for the presence of recessive genes for fertility restoration. The agronomic properties of the key plants may be improved through well-known plant breeding techniques. A cross between the cytoplasmic male sterile plants and the maintainer plants is always cytoplasmic male sterile, and will exhibit either Type A or Type B herbicide tolerance, depending upon the nature of the cytoplasm and the presence or absence of the required nuclear genes for such Type B tolerance. Once a maintainer plant is located it must be multiplied by self-pollination, or optionally by clonal propagation.

The restorer plants which are capable of pollinating the plants which exhibit cytoplasmic male sterility must possess either Type A herbicide tolerance or Type B herbicide tolerance, depending upon the process embodiment in which they are utilized. If the maintainer plants exhibit Type A herbicide tolerance, the restorer plants will exhibit Type B herbicide tolerance to a different herbicide which is lacking in the maintainer plants. If the maintainer plants lack Type A herbicide tolerance, the restorer plants will exhibit Type B herbicide tolerance to a different herbicide which is lacking in the maintainer plants. These plants must, by necessity, be homozygous restorers with respect to the dominant fertility restorer genes which interact with the requisite cytoplasm. Because of the dominant transmission mode for fertility restoration these plants often are far more common than the maintainer plants in a given plant population.

The article appearing in the *Canadian Journal of Genetics and Cytology*, Volume XXII, No. 2, June 1980, by W. D. Beversdorf, J. Weiss-Lerman, L. R. Erickson and V. Souza Machado entitled, "Transfer of Cytoplasmically-Inherited Triazine Resistance from Bird's Rape to Cultivated Rape (*Brassica campestris* and *B. napus*)", discusses a route whereby one may obtain cytoplasmic tolerance for a herbicide in the named plants of agronomic importance. More specifically, it initially was observed that a weed biotype of *Brassica campestris* known as bird's rape infested a corn field near Brampton, Quebec, Canada, in spite of prolonged applications of conventional triazine herbicides. Accordingly, this weed biotype was deemed to be tolerant to at least seven s-triazine herbicides including atrazine as described. This triazine tolerance through controlled backcrossing techniques was transferred to known cultivars of oilseed rape (i.e., *Brassica campestris* and *Brassica napus*) to provide improved oilseed rape cultivars which could be used in weed control programs. More specifically, during flowering crosses were made between emasculated flowers of bird's rape and oilseed rape cultivars (e.g., Tower cultivar). It was found that all backcross progeny from (bird's rape X cultivar) X cultivar were resistant to an application of atrazine while all backcross progeny from (cultivar X bird's rape) X cultivar were killed by the atrazine application, as were the cultivar controls. The results accordingly indicated that the atrazine resistance had been cytoplasmically inherited.

Samples of the resulting herbicides tolerant *Brassica napus* seed previously have been released to the public by the Crop Science Department, Ontario Agricultural College, University of Guelph, Ontario, Canada, under the designation of Reg. No. GP 2, and Catalogue No. ATR-5TW in its 1980 and 1983 Germ Plasm Releases. In this regard also see "Registration of Triazine Resistant *Brassica Napus* Germplasm" which appeared in Crop Science, Vol. 20, March-April 1980, page 289. Also, herbicide tolerant *Brassica napus* seed from this program has been deposited in the National Seed Storage Laboratory at Fort Collins, Colo., USA under our Sample No. ATR-5Tw, Laboratory Accession No. BNa-21, and Serial No. 180171. Such seed identified above is capable of growing plants which are all fully male fertile. The use of seed having such herbicide tolerance will enable the growing of a commercial rape crop in which weeds such as stinkweed (*Thlaspi arvense*, L.) and wild mustard (*Brassica kaber* D. C. Wheeler) could be readily eliminated without harm to the commercial crop.

As reported in our U.S. Pat. No. 4,517,763, (which is herein incorporated by reference), we have subsequently discovered that rape plants which express cytoplasmic male sterility may be developed from ATR-5Tw which possesses the requisite cytoplasmic herbicide tolerance. This was accomplished by crossing such *Brassica napus* cytoplasmic herbicide tolerant rape backcrosses while serving as the female parent with pollen from a male parent of a cultivar of *Brassica napus* known as Bronowski, which has been found to be highly variable with respect to recessive genes for fertility restoration, and subsequently carrying out enforced selfing to the $F_2$ generation. The $F_2$ plants which exhibited reduced male fertility were next visually selected and isolated. Such plants were partially male sterile and were heterozygous with respect to the genes for fertility restoration. Enforced self-pollination of the partially male sterile plants resulted in the production of fully male sterile plants which were characterized by the complete absence of pollen. Such plants were found to exhibit cytoplasmic male sterility as well as atrazine tolerance and to be totally homozygous recessive with respect to nuclear fertility restoring genes. In the absence of the usual dominant fertility restoring genes the cytoplasm uniformly manifests male sterility in addition to the atrazine herbicide tolerance. The agronomic properties have been improved through well-known backcross techniques. Such plants exhibit cytoplasmic atrazine tolerance when applied as a foliar spray at a rate of 2 kilograms per hectare. To such male sterile plants may be introduced (e.g., by conventional plant breeding) the homozygous nuclear genes (i.e., either homozygous dominant or homozygous recessive) which will impart tolerance to at least one Type A herbicide. Such genes may be similarly introduced into either maintainer or restorer plants for the same.

As will be apparent to those skilled in plant breeding, there are several different cytoplasmic male sterile systems available in *Brassica napus*, and a given rape cultivar can be a maintainer or a restorer depending upon the system which is selected. Maintainer plants for the POL and OGU cytoplasmic systems are found in virtually all *Brassica napus* cultivars and accordingly are simple to identify by test-crossing. Maintainer plants for the NAP cytoplasmic system have been isolated in the Bronowski and Isuzunatane cultivars of *Brassica napus*. Maintainer plants for the CTR cytoplasmic system have been isolated in the Bronowski cultivar of *Brassica napus*.

Restorer plants for the POL and OGU cytoplasmic systems can be the Italy cultivar of *Brassica napus* and the Zem cultivar of *Brassica juncea*. In the NAP and CTR cytoplasmic systems virtually all *Brassica napus* cultivars are restorers and may be readily located by simple test crosses.

As indicated herein, the process of the present invention makes possible the highly economical bulk planting of the parent plants during each step of the process. Following the crossing of the cytoplasmic male sterile plants with pollen from the maintainer plants while grown in bulk, one next grows in a substantially random population (1) the required cytoplamic male sterile plants, (2) plants resulting from the self-pollination of the maintainer plants, and (3) restorer plants. The plants resulting from the self-pollination of a maintainer initially are destroyed prior to pollination by contact with appropriate herbicide (i.e., either a Type A or a Type B herbicide), and self-pollinated restorer plants are destroyed by a different herbicide of the other type following pollination or in the subsequent generation. One thereby produces either (1) seed capable of forming a predetermined hybrid variety of crop in the substantial absence of seed from the maintainer and restorer plants or (2) a substantially homogeneous population of plants of a predetermined variety of crop. When the product is seed capable of growing an $F_1$ hybrid crop, this seed is next harvested. Conventional planting techniques may be employed while forming a random mixtures of the two and three plant components. There is no requirement that equal quantities of the male and female parents be employed. For instance, the seeds capable of forming the cytoplasmic male sterile plants which serve as the seed parent commonly will be provided in the major amount. Accordingly, such seed will commonly comprise 60 to 90 percent or more of the total amount of seed which is initially planted with maintainer plants. A similar proportion also may be employed in a subsequent process step with seed for restorer plants while disregarding seed derived from the maintainer plants. Accordingly, one male fertile plant can commonly pollinate more than one male sterile plant. As will be apparent to those skilled in seed production technology, the relative proportions of the two plant types should be adjusted so as to achieve the desired level of pollination on a consistent basis while utilizing the minimum quantity of male fertile plants.

When the maintainer plants lack Type A herbicide tolerance and exhibit Type B herbicide tolerance, the cytoplasmic male sterile plants readily can be maintained for two or more generations as random plantings in a preliminary planting area (i.e., prior to use of the first planting area) in accordance with an embodiment of the present invention. The resulting seeds can be harvested in bulk and replanted in bulk in the first planting area together with maintainer plants which exhibit Type A herbicide tolerance, and a Type A herbicide next applied following pollination to destroy maintainer plants derived from seed formed in the preliminary planting area. In such embodiment the restorer plants subsequently utilized exhibit the Type B herbicide tolerance.

The present invention provides for the first time the ability to form a *Brassica napus* seed product consisting of a substantially homogeneous assemblage of seeds which upon growth yield rape plants which exhibit a combination of cytoplasmic male sterility, cytoplasmic tolerance to at least one herbicide, and tolerance to at least one different herbicide which is attributable solely to homozygous nuclear genes (i.e. either homozygous dominant or homozygous recessive genes).

Also, for the first time a *Brassica napus* seed product is provided consisting of a substantially homogeneous assemblage of seeds which upon growth yield male fertile $F_1$ hybrid rape plants which exhibit cytoplasmic tolerance to at least one herbicide, and tolerance to at least one different herbicide which is attributable solely to nuclear genes.

Although the invention has been described with preferred embodiments, it is to be understood that variations and modifications may be resorted to as will be apparent to those skilled in the art. Such variations and modifications are to be considered within the purview and scope of the claims appended hereto.

We claim:
1. An improved process for producing a substantially homogeneous population of plants of a predetermined hybrid variety of crop which is capable of undergoing self-pollination and cross-pollination comprising:
   (a) growing in a first planting area a substantially random population of (1) cytoplasmic male sterile plants which exhibit cytoplasmic herbicide tolerance to at least one Type A herbicide and exhibit tolerance to at least one Type B herbicide which is attributable solely to homozygous dominant nuclear genes, and (2) male fertile plants which are homozygous recessive maintainer plants for said cytoplasmic male sterile plants and which lack said cytoplasmic herbicide tolerance to at least one Type A herbicide and exhibit tolerance to said at least one Type B herbicide attributable solely to said homozygous dominant nuclear genes, whereby said cytoplasmic male sterile plants (1) and said maintainer plants are pollinated with pollen derived from said maintainer plants and seed is formed on said cytoplasmic male sterile plants and on said maintainer plants,
   (b) harvesting in bulk the seed which is formed on said plants of said first planting area,
   (c) growing in a second planting area a substantially random population of plants derived from seed harvested in step (b) together with homozygous dominant fertility restorer plants for said cytoplasmic male sterile plants which exhibit cytoplasmic herbicide tolerance to said at least one Type A herbicide and lack tolerance to said at least one Type B herbicide because of the absence of the required dominant nuclear genes for such trait,
   (d) contacting prior to pollination substantially all of the plants present in said second planting area with a Type A herbicide which is effective to destroy the plants resulting from seed formed on said maintainer plants in step (a) whereby cytoplasmic male sterile plants and restorer plants remain,
   (e) pollinating said cytoplasmic male sterile plants and said restorer plants of step (d) with pollen derived from said restorer plants and seed is formed on said cytoplasmic male sterile plants and on said restorer plants, (f) harvesting in bulk the seed which is formed on said plants remaining in said second planting area, (g) growing in a third planting area a substantially random population of plants derived from seed harvested in step (f), and (h) contacting substantially all of the plants present in said third planting area with a Type B herbicide which is effective to destroy said plants resulting from the seed formed on said restorer plants of step (e), whereby a substantially homogeneous population of male fertile $F_1$ hybrid plants of a predetermined variety is formed.

2. An improved process for producing a substantially homogeneous population of plants of a predetermined hybrid variety of a crop according to claim 1 wherein said crop is selected from the group consisting of grain crops, forage crops, seed-propagated fruits, seed-propagated ornamentals, and industrial species.

3. An improved process for producing a substantially homogeneous population of plants of a predetermined hybrid variety of crop according to claim 1 wherein said crop is of the family Brassicaceae.

4. An improved process for producing a substantially homogeneous population of plants of a predetermined hybrid variety of crop according to claim 1 wherein said crop is of the genus Brassica.

5. An improved process for producing a substantially homogeneous population of plants of a predetermined hybrid variety of crop according to claim 1 wherein said crop is *Brassica napus*.

6. An improved process for producing a substantially homogeneous population of plants of a predetermined hybrid variety of crop according to claim 1 wherein said crop is *Brassica campestris*.

7. An improved process for producing a substantially homogeneous population of plants of a predetermined hybrid variety of crop according to claim 1 wherein prior to step (a) steps identical to steps (a) and (b) are repeated at least one time in order to obtain the seed which is grown in said first planting area of step (a).

8. An improved process for producing a substantially homogeneous population of plants of a predetermined hybrid variety of crop according to claim 1 which includes the additional step of (i) harvesting seed which forms on said male fertile $F_1$ hybrid plants as a result of self-pollination.

9. An improved process for producing a substantially homogeneous population of plants of a predetermined hybrid variety of crop according to claim 1 wherein said pollination takes place with the aid of pollen-carrying insects.

10. An improved process for producing a substantially homogeneous population of plants of a predetermined hybrid variety of crop according to claim 1 wherein said Type A herbicide operates by inhibiting photosynthesis.

11. An improved process for producing a substantially homogeneous population of plants of a predetermined hybrid variety of crop according to claim 1 wherein said Type A herbicide is selected from the group consisting of s-triazines and as-triazines.

12. An improved process for producing a substantially homogeneous population of plants of a predetermined hybrid variety of crop according to claim 1 wherein said Type A herbicide is atrazine.

13. An improved process for producing a substantially homogeneous population of plants of a predetermined hybrid variety of crop according to claim 1 wherein said Type A herbicide is cyanazine.

14. An improved process for producing a substantially homogeneous population of plants of a predetermined hybrid variety of crop according to claim 1 wherein said Type B herbicide is selected from the group consisting of sulfonylureas, glycine derivatives, and imidazolinones.

15. An improved process for producing a substantially homogeneous population of plants of a predetermined hybrid variety of crop according to claim 1 wherein said Type B herbicide is chlorsulfuron.

16. An improved process for producing a substantially homogeneous population of plants of a predetermined hybrid variety of crop according to claim 1 wherein said Type B herbicide is glyphosate.

17. An improved process for producing a substantially homogeneous population of plants of a predetermined hybrid variety of crop according to claim 1 wherein said Type B herbicide is amitrole.

18. An improved process for producing a substantially homogeneous population of plants of a predetermined hybrid variety of crop according to claim 1 wherein said Type B herbicide is bentazon.

19. An improved process for producing seed capable of forming a predetermined hybrid variety of a crop which is capable of undergoing both self-pollination and cross-pollination comprising:

(a) growing in a first planting area a substantially random population of (1) cytoplasmic male sterile plants which exhibit cytoplasmic herbicide tolerance to at least one Type A herbicide and exhibit tolerance to at least one Type B herbicide which is attributable solely to homozygous dominant nuclear genes, and (2) male fertile plants which are homozygous recessive maintainer plants for said cytoplasmic male sterile plants and which lack said cytoplasmic herbicide tolerance to at least one Type A herbicide and exhibit tolerance to said at least one Type B herbicide attributable solely to said homozygous dominant nuclear genes, whereby said cytoplasmic male sterile plants (1) and said maintainer plants are pollinated with pollen derived from said maintainer plants and seed is formed on said cytoplasmic male sterile plants and on said maintainer plants, (b) harvesting in bulk the seed which is formed on said plants of said first planting area, (c) growing in a second planting area a substantially random population of plants derived from seed harvested in step (b) together with homozygous dominant fertility restorer plants for said cytoplasmic male sterile plants which exhibit cytoplasmic herbicide tolerance to said at least one Type A herbicide and lack tolerance to said at least one Type B herbicide because of the absence of the required dominant nuclear genes for such trait, (d) contacting prior to pollination substantially all of the plants present in said second planting area with a Type A herbicide which is effective to destroy the plants resulting from seed formed on said maintainer plants in step (a) whereby cytoplasmic male sterile plants and restorer plants remain, (e) pollinating said cytoplasmic male sterile plants and said restorer plants of step (d) with pollen derived from said restorer plants, (f) subsequently contacting substantially all of the remaining plants present in said second planting area with a Type B herbicide which is effective to destroy said restorer plants and which is ineffective to destroy cytoplasmic male sterile plants because of said herbicide tolerance attributable solely to said homozygous nuclear genes, and (g) harvesting seed from said cytoplasmic male sterile plants which is capable of forming $F_1$ hybrid plants which exhibit tolerance to each of said Type A and Type B herbicide in the substantial absence of seed from said maintainer and restorer plants which initially grew in said second planting area.

20. An improved process for producing seed capable of forming a predetermined hybrid variety of a crop according to claim 19 wherein said crop is selected from the group consisting of grain crops, forage crops, seed-propagated fruits, seed-propagated ornamentals, and industrial species.

21. An improved process for producing seed capable of forming a predetermined hybrid variety of crop according to claim 19 wherein said crop is of the family Brassicaceae.

22. An improved process for producing seed capable of forming a predetermined hybrid variety of crop according to claim 19 wherein said crop is of the genus Brassica.

23. An improved process for producing seed capable of forming a predetermined hybrid variety of crop according to claim 19 wherein said crop is of the genus *Brassica napus.*

24. An improved process for producing seed capable of forming a predetermined hybrid variety of crop according to claim 19 wherein said crop is of the genus *Brassica campestris.*

25. An improved process for producing seed capable of forming a predetermined hybrid variety of crop according to claim 19 wherein prior to step (a) steps identical to steps (a) and (b) are repeated at least one time in order to obtain the seed which is grown in said first planting area of step (a).

26. An improved process for producing seed capable of forming a predetermined hybrid variety of crop according to claim 19 wherein said pollination takes place with the aid of pollen-carrying insects.

27. An improved process for producing seed capable of forming a predetermined hybrid variety of a crop according to claim 19 wherein said Type A herbicide operates by inhibiting photosynthesis.

28. An improved process for producing seed capable of forming a predetermined hybrid variety of a crop according to claim 19 wherein said Type A herbicide is selected from the group consisting of s-triazines and as-triazines.

29. An improved process for producing seed capable of forming a predetermined hybrid variety of a crop according to claim 19 wherein said Type A herbicide is atrazine.

30. An improved process for producing seed capable of forming a predetermined hybrid variety of a crop according to claim 19 wherein said Type A herbicide is cyanazine.

31. An improved process for producing a substantially homogeneous population of plants of a predetermined hybrid variety of a crop according to claim 19 wherein said Type B herbicide is selected from the group consisting of sulfonylureas, glycine derivatives and imidazolinones.

32. An improved process for producing seed capable of forming a predetermined hybrid variety of a crop according to claim 19 wherein said Type B herbicide is chlorsulfuron.

33. An improved process for producing seed capable of forming a predetermined hybrid variety of a crop according to claim 19 wherein said Type B herbicide is glyphosate.

34. An improved process for producing seed capable of forming a predetermined hybrid variety of a crop according to claim 19 wherein said Type B herbicide is amitrole.

35. An improved process for producing seed capable of forming a predetermined hybrid variety of a crop according to claim 19 wherein said Type B herbicide is bentazon.

36. An improved process for producing a substantially homogeneous population of plants of a predetermined hybrid variety of a crop which is capable of undergoing both self-pollination and cross-pollination comprising:

(a) growing in a first planting area a substantially random population of (1) cytoplasmic male sterile plants which exhibit cytoplasmic herbicide tolerance to at least one Type A herbicide and exhibit tolerance to at least one Type B herbicide which is attributable solely to homozygous nuclear genes, and (2) male fertile plants which are homozygous recessive maintainer plants for said cytoplasmic male sterile plants and which exhibit said cytoplasmic herbicide tolerance to at least one Type A herbicide and lack said tolerance to said at least one Type B herbicide because of the absence of the required nuclear genes for such trait, whereby said cytoplasmic male sterile plants (1) and said maintainer plants are pollinated with pollen derived from said maintainer plants and seed is formed on said cytoplasmic male sterile plants and on said maintainer plants, (b) harvesting in bulk the seed which is formed on said plants of said first planting area, (c) growing in a second planting area a substantially random population of plants derived from seed harvested in step (b) together with homozygous dominant fertility restorer plants for said cytoplasmic male sterile plants which lack said cytoplasmic herbicide tolerance to said at least one Type A herbicide and exhibit tolerance to said at least one Type B herbicide because of the presence of said required homozygous nuclear genes for such trait, (d) contacting prior to pollination substantially all of the plants present in said second planting area with a Type B herbicide which is effective to destroy the plants resulting from seed formed on said maintainer plants in step (a) whereby cytoplasmic male sterile plants and restorer plants remain, (e) pollinating said cytoplasmic male sterile plants and said restorer plants of step (d) with pollen derived from said restorer plants and seed is formed on said cytoplasmic male sterile plants and on said restorer plants, (f) harvesting in bulk the seed which is formed on said plants remaining in said second planting area, (g) growing in a third planting area a substantially random population of plants derived from seed harvested in step (f), and (h) contacting substantially all of the plants present in said third planting area with a Type A herbicide which is effective to destroy said plants resulting from the seed formed on said restorer plants of step (e), whereby a substantially homogeneous population of male fertile F₁ hybrid plants of a predetermined variety is formed.

37. An improved process for producing a substantially homogeneous population of plants of a predetermined hybrid variety of a crop according to claim 36 wherein said crop is selected from the group consisting of grain crops, forage crops, seed-propagated fruits, seed-propagated ornamentals, and industrial species.

38. An improved process for producing a substantially homogeneous population of plants of a predetermined hybrid variety of crop according to claim 36 wherein said crop is of the family Brassicaceae.

39. An improved process for producing a substantially homogeneous population of plants of a predetermined hybrid variety of crop according to claim 36 wherein said crop is of the genus Brassica.

40. An improved process for producing a substantially homogeneous population of plants of a predetermined hybrid variety of crop according to claim 36 wherein said crop is *Brassica napus*.

41. An improved process for producing a substantially homogeneous population of plants of a predetermined hybrid variety of crop according to claim 36 wherein said crop is *Brassica campestris*.

42. An improved process for producing a substantially homogeneous population of plants of a predetermined hybrid variety of crop according to claim 36 wherein prior to step (a) the following process steps additionally are practiced:
  (i) growing in a preliminary planting area a substantially random population of cytoplasmic male sterile plants which exhibit cytoplasmic herbicide tolerance to at least one Type A herbicide and exhibit tolerance to at least one Type B herbicide which is attributable solely to homozygous nuclear genes, and male fertile plants which are homozygous recessive maintainer plants for said cytoplasmic male sterile plants and which lack said cytoplasmic herbicide tolerance to at least one Type A herbicide and exhibit tolerance to said at least one Type B herbicide attributable solely to said homozygous nuclear genes, whereby said cytoplasmic male sterile plants and said maintainer plants are pollinated with pollen derived from said maintainer plants and seed is formed on said cytoplasmic male sterile plants and on said maintainer plants,
  (ii) harvesting in bulk the seed which is formed on said plants of said preliminary planting area,
  (iii) growing in the first planting area of step (a) a substantially random population of plants derived from seed harvested in step (ii) together with the male fertile maintainer plants (2) of step (a), and
  (iv) contacting prior to pollination substantially all of the plants present in said first planting area of step (a) with a Type A herbicide which is effective to destroy the plants resulting from seed formed on said maintainer plants in step (i) whereby cytoplasmic male sterile plants (1) and the male fertile maintainer plants (2) of step (a) remain.

43. An improved process for producing a substantially homogeneous population of plants of a predetermined hybrid variety of crop according to claim 42 wherein steps (i) and (ii) are repeated at least one time prior to step (iii) with the product of step (ii) serving as the source of the seed which is planted in step (i).

44. An improved process for producing a substantially homogeneous population of plants of a predetermined hybrid variety of crop according to claim 36 which includes the additional step of:
  (i) harvesting seed which forms on said male fertile F₁ hybrid plants as a result of self-pollination 45. An improved process for producing a substantially homogeneous population of plants of a predetermined hybrid variety of crop according to claim 36 wherein said pollination takes place with the aid of pollen-carrying insects.

46. An improved process for producing a substantially homogeneous population of plants of a predetermined hybrid variety of crop according to claim 36 wherein said cytoplasmic male sterile plants (1) of step (a) and said restorer plants of step (c) each exhibit tolerance to said at least one Type B herbicide which is attributable solely to homozygous dominant nuclear genes, and the resulting F₁ hybrid plants of step (h) exhibit tolerance to each of said Type A and Type B herbicides.

47. An improved process for producing a substantially homogeneous population of plants of a predetermined hybrid variety of crop according to claim 36 wherein said cytoplasmic male sterile plants (1) of step (a) and said restorer plants of step (c) each exhibit tolerance to said at least one Type B herbicide which is attributable solely to homozygous recessive nuclear genes, and resulting F₁ hybrid plants of step (h) exhibit tolerance to said Type A herbicide and lack tolerance to said Type B herbicide.

48. An improved process for producing a substantially homogeneous population of plants of a predetermined hybrid variety of crop according to claim 36 wherein said Type A herbicide operates by inhibiting photosynthesis.

49. An improved process for producing a substantially homogeneous population of plants of a predetermined hybrid variety of crop according to claim 36 wherein said Type A herbicide is selected from the group consisting of s-triazines and as-triazines.

50. An improved process for producing a substantially homogeneous population of plants of a predetermined hybrid variety of crop according to claim 36 wherein said Type A herbicide is atrazine.

51. An improved process for producing a substantially homogeneous population of plants of a predetermined hybrid variety of crop according to claim 36 wherein said Type A herbicide is cyanazine.

52. An improved process for producing a substantially homogeneous population of plants of a predetermined hybrid variety of crop according to claim 36 wherein said Type B herbicide is selected from the group consisting of sulfonylureas, glycine derivatives, and imidazolinones.

53. An improved process for producing a substantially homogeneous population of plants of a predetermined hybrid variety of crop according to claim 36 wherein said Type B herbicide is chlorsulfuron.

54. An improved process for producing a substantially homogeneous population of plants of a predetermined hybrid variety of crop according to claim 36 wherein said Type B herbicide is glyphosate.

55. An improved process for producing a substantially homogeneous population of plants of a predetermined hybrid variety of crop according to claim 36 wherein said Type B herbicide is amitrole.

56. An improved process for producing a substantially homogeneous population of plants of a predetermined hybrid variety of crop according to claim 36 wherein said Type B herbicide is bentazon.

57. An improved process for producing seed capable of forming a predetermined hybrid variety of a crop which is capable of undergoing both self-pollination and cross-pollination comprising:

(a) growing in a first planting area a substantially random population of (1) cytoplasmic male sterile plants which exhibit cytoplasmic herbicide tolerance to at least one Type A herbicide and exhibit tolerance to at least one Type B herbicide which is attributable solely to homozygous nuclear genes, and (2) male fertile plants which are homozygous recessive maintainer plants for said cytoplasmic male sterile plants and which exhibit said cytoplasmic herbicide tolerance to at least one Type A herbicide and lack said tolerance to said at least one Type B herbicide because of the absence of the required nuclear genes for such trait, whereby said cytoplasmic male sterile plants (1) and said maintainer plants are pollinated with pollen derived from said maintainer plants and seed is formed on said cytoplasmic male sterile plants and on said maintainer plants, (b) harvesting in bulk the seed which is formed on said plants of said first planting area, (c) growing in a second planting area a substantially random population of plants derived from seed harvested in step (b) together with homozygous dominant fertility restorer plants for said cytoplasmic male sterile plants which lack said cytoplasmic herbicide tolerance to said at least one Type A herbicide and exhibit tolerance to said at least one Type B herbicide because of the presence of said required homozygous nuclear genes for such trait, (d) contacting prior to pollination substantially all of the plants present in said second planting area with a Type B herbicide which is effective to destroy the plants resulting from seed formed on said maintainer plants in step (a) whereby cytoplasmic male sterile plants and restorer plants remain, (e) pollinating said cytoplasmic male sterile plants and said restorer plants of step (d) with pollen derived from said restorer plants and seed is formed on said cytoplasmic male sterile plants and on said restorer plants, (f) subsequently contacting substantially all of the remaining plants present in said second planting area with a Type A herbicide which is effective to destroy said restorer plants and which is ineffective to destroy said cytoplasmic male sterile plants because of said herbicide tolerance attributable solely to said homozygous nuclear genes, and (g) harvesting seed from said cytoplasmic male sterile plants which is capable of forming $F_1$ hybrid plants in the substantial absence of seed from said maintainer and restorer plants which initially grew in said second planting area.

58. An improved process for producing seed capable of forming a predetermined hybrid variety of a crop according to claim 57 wherein said crop is selected from the group consisting of grain crops, forage crops, seed-propagated fruits, seed-propagated ornamentals, and industrial species.

59. An improved process for producing seed capable of forming a predetermined hybrid variety of a crop according to claim 57 wherein said crop is of the family Brassicaceae.

60. An improved process for producing seed capable of forming a predetermined hybrid variety of a crop according to claim 57 wherein said crop is of the genus Brassica.

61. An improved process for producing seed capable of forming a predetermined hybrid variety of a crop according to claim 57 wherein said crop is *Brassica napus*.

62. An improved process for producing seed capable of forming a predetermined hybrid variety of a crop according to claim 57 wherein said crop is *Brassica campestris*.

63. An improved process for producing seed capable of forming a predetermined hybrid variety of a crop according to claim 57 wherein prior to step (a) the following process steps additionally are practiced:

(i) growing in a preliminary planting area a substantially random population of cytoplasmic male sterile plants which exhibit cytoplasmic herbicide tolerance to at least one Type A herbicide and exhibit tolerance to at least one Type B herbicide which is attributable solely to homozygous nuclear genes, and male fertile plants which are homozygous recessive maintainer plants for said cytoplasmic male sterile plants and which lack said cytoplasmic herbicide tolerance to said at least one Type A herbicide and exhibit tolerance to said at least one Type B herbicide attributable solely to said homozygous nuclear genes, whereby said cytoplasmic male sterile plants and said maintainer plants are pollinated with pollen derived from said maintainer plants and seed is formed on said cytoplasmic male sterile plants and on said maintainer plants, (ii) harvesting in bulk the seed which is formed on said plants of said preliminary planting area, (iii) growing in the first planting area of step (a) a substantially random population of plants derived from seed harvested in step (ii) together with the male fertile maintainer plants (2) of step (a), and (iv) contacting prior to pollination substantially all of the plants present in said first planting area of step (a) with a Type A herbicide which is effective to destroy the plants resulting from seed formed on said maintainer plants in step (i) whereby cytoplasmic male sterile plants (1) and the male fertile maintainer plants (2) of step (a) remain.

64. An improved process for producing seed capable of forming a predetermined hybrid variety of a crop according to claim 63 wherein steps (i) and (ii) are repeated at least one time prior to step (iii) with the product of step (ii) serving as the source of the seed which is planted in step (i).

65. An improved process for producing seed capable of forming a predetermined hybrid variety of a crop according to claim 57 wherein said pollination takes place with the aid of pollen-carrying insects.

66. An improved process for producing seed capable of forming a predetermined hybrid variety of a crop according to claim 57 wherein said cytoplasmic male sterile plants (1) of step (a) and said restorer plants of step (c) each exhibit tolerance to said at least one Type B herbicide which is attributable solely to homozygous dominant nuclear genes, and the seed harvested in step (g) is capable of forming $F_1$ hybrid plants which exhibit tolerance to said Type A and Type B herbicides.

67. An improved process for producing seed capable of forming a predetermined hybrid variety of a crop according to claim 57 wherein said cytoplasmic male sterile plants (1) of step (a) and said restorer plants of step (c) each exhibit tolerance to said at least one Type B herbicide which is attributable solely to homozygous recessive nuclear genes, and the seed harvested in step (g) is capable of forming $F_1$ hybrid plants which exhibit tolerance to said Type A herbicide and a lack of tolerance to said Type B herbicide.

68. An improved process for producing seed capable of forming a predetermined hybrid variety of a crop according to claim 57 wherein said Type A herbicide operates by inhibiting photosynthesis.

69. An improved process for producing seed capable of forming a predetermined hybrid variety of a crop according to claim 57 wherein said Type A herbicide is selected from the group consisting of s-triazines and as-triazines.

70. An improved process for producing seed capable of forming a predetermined hybrid variety of a crop according to claim 57 wherein said Type A herbicide is atrazine.

71. An improved process for producing seed capable of forming a predetermined hybrid variety of a crop according to claim 57 wherein said Type A herbicide is cyanazine.

72. An improved process for producing seed capable of forming a predetermined hybrid variety of a crop according to claim 57 wherein said Type B herbicide is selected from the group consisting essentially of sulfonylureas, glycine derivatives, and imidazolinones.

73. An improved process for producing seed capable of forming a predetermined hybrid variety of a crop according to claim 57 wherein said Type B herbicide is chlorsulfuron.

74. An improved process for producing seed capable of forming a predetermined hybrid variety of a crop according to claim 57 wherein said Type B herbicide is glyphosate.

75. An improved process for producing seed capable of forming a predetermined hybrid variety of a crop according to claim 57 wherein said Type B herbicide is amitrole.

76. An improved process for producing seed capable of forming a predetermined hybrid variety of a crop according to claim 57 wherein said Type B herbicide is bentazon.

77. A *Brassica napus* seed product consisting of a substantially homogeneous assemblage of seeds which upon growth yield rape plants which exhibit a combination of cytoplasmic male sterility, cytoplasmic tolerance to at least one herbicide, and tolerance to at least one different herbicide which is attributable solely to homozygous dominant nuclear genes.

78. A *Brassica napus* seed product consisting of a substantially homogeneous assemblage of seeds which upon growth yield rape plants which exhibit a combination of cytoplasmic male sterility, cytoplasmic tolerance to at least one herbicide, and tolerance to at least one different herbicide which is attributable solely to homozygous recessive nuclear genes.

79. A *Brassica napus* seed product consisting of a substantially homogeneous assemblage of seeds which upon growth yield male fertile $F_1$ hybrid rape plants which exhibit cytoplasmic tolerance to at least one herbicide, and tolerance to at least one different herbicide which is attributable solely to nuclear genes.

* * * * *